(12) United States Patent
Czeizler et al.

(10) Patent No.: US 11,813,479 B2
(45) Date of Patent: Nov. 14, 2023

(54) METHOD AND APPARATUS TO FACILITATE ADMINISTERING THERAPEUTIC RADIATION TO A PATIENT

(71) Applicant: Siemens Healthineers International AG, Steinhausen (CH)

(72) Inventors: Elena Czeizler, Helsinki (FI); Esa Kuusela, Espoo (FI); Mikko Hakala, Helsinki (FI); Shahab Basiri, Helsinki (FI)

(73) Assignee: Siemens Healthineers International AG, Steinhausen (CH)

(*) Notice: Subject to any disclaimer, the term of this patent is extended or adjusted under 35 U.S.C. 154(b) by 247 days.

(21) Appl. No.: 16/898,643

(22) Filed: Jun. 11, 2020

(65) Prior Publication Data
US 2021/0387017 A1    Dec. 16, 2021

(51) Int. Cl.
*A61N 5/10* (2006.01)
*G06T 7/00* (2017.01)
*G06T 9/20* (2006.01)
*G06T 9/00* (2006.01)

(52) U.S. Cl.
CPC .......... *A61N 5/1031* (2013.01); *G06T 7/0012* (2013.01); *G06T 9/002* (2013.01); *G06T 9/004* (2013.01); *G06T 9/20* (2013.01); *G06T 2207/10081* (2013.01); *G06T 2207/20084* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 9,827,445 B2* | 11/2017 | Cordero Marcos | G16H 20/40 |
| 10,850,121 B2* | 12/2020 | Moore | A61N 5/1031 |
| 2013/0142310 A1 | 6/2013 | Fahimian | |
| 2018/0243584 A1 | 8/2018 | Nord | |
| 2018/0243586 A1* | 8/2018 | Ramezanzadeh Moghadam | G16H 20/40 |
| 2019/0030370 A1* | 1/2019 | Hibbard | A61N 5/1067 |

FOREIGN PATENT DOCUMENTS

WO    2018048575 A1    3/2018

OTHER PUBLICATIONS

Nguyen, Dan et al.; Dose Prediction with U-net: A Feasibility Study for Predicting Dose Distributions from Contours Using Deep Learning on Prostate IMRT Patients; Published 2017; arXiv preprint arXiv:1709.09233; 17 pages.

Fan, Jiawei et al.; Automatic Treatment Planning Based on Three-Dimensional Dose Distribution Predicted from Deep Learning Technique; first published Nov. 2018 in American Association of Physicists in Medicine, https://doi.org/10.102/mp.13271; Medical Physics 46(1), Jan. 2019, pp. 370-381.

(Continued)

*Primary Examiner* — James A Thompson
(74) *Attorney, Agent, or Firm* — Fitch, Even, Tabin & Flannery LLP

(57) ABSTRACT

A control circuit accesses patient image content as well as field geometry information regarding a particular radiation treatment platform. The control circuit then generates a predicted three-dimensional dose map for the radiation treatment plan as a function of both the patient image content and the field geometry information.

20 Claims, 3 Drawing Sheets

(56) References Cited

OTHER PUBLICATIONS

Kearney, Vasant et al.; DoseNet: a Volumetric Dose Prediction Algorithm Using 3D Fully-Convolutional Neural Networks; Physics in Medicine & Biology, 63(23) Dec. 2018; IOP Publishing; 12 pages.

International Search Report and Written Opinion from related Application No. PCT/EP2021/065720 dated Sep. 24, 2021; 12 pages.

* cited by examiner

METHOD AND APPARATUS TO FACILITATE ADMINISTERING THERAPEUTIC RADIATION TO A PATIENT

TECHNICAL FIELD

These teachings relate generally to treating a patient's planning target volume with radiation pursuant to a radiation treatment plan and more particularly to predicted dose maps that correspond to radiation treatment plans.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects.

Recent advancements in radiation treatment planning have improved the overall quality of the plans and ultimately led to better patient outcomes. Unfortunately, these advancements have also led to an increase in treatment plan complexity and the time required to formulate the radiation treatment plan. Obtaining optimal plans for a given patient can depend heavily on the planner's expertise and often requires several iterative interactions between the planner and the oncologist. To decrease both planning time and variation in treatment plan quality, some prior art approaches seek to automate at least a part of the planning process.

Such attempts at automation include the use of artificial intelligence to accomplish such things as organ segmentation, tumor identification, and three-dimensional dose prediction. Three-dimensional dose prediction refers to predicting the likely radiation dosage that will occur at various locations within a planning target volume and/or one or more organs-at-risk in the patient upon treating the patient per a given radiation treatment plan. Unfortunately, training an artificial intelligence model can be very challenging when using heterogeneous patient data with variations in the position, shape, and size of the planning treatment volume as well as the type of treatment (e.g., sided/full arc, coplanar/non-coplanar, and so forth). Variations in field geometry can present even greater challenges when the three-dimensional dose prediction is done for one individual two-dimensional slice at a time.

BRIEF DESCRIPTION OF THE DRAWINGS

The above needs are at least partially met through provision of the method and apparatus to facilitate administering therapeutic radiation to a patient described in the following detailed description, particularly when studied in conjunction with the drawings, wherein.

Figure 1:
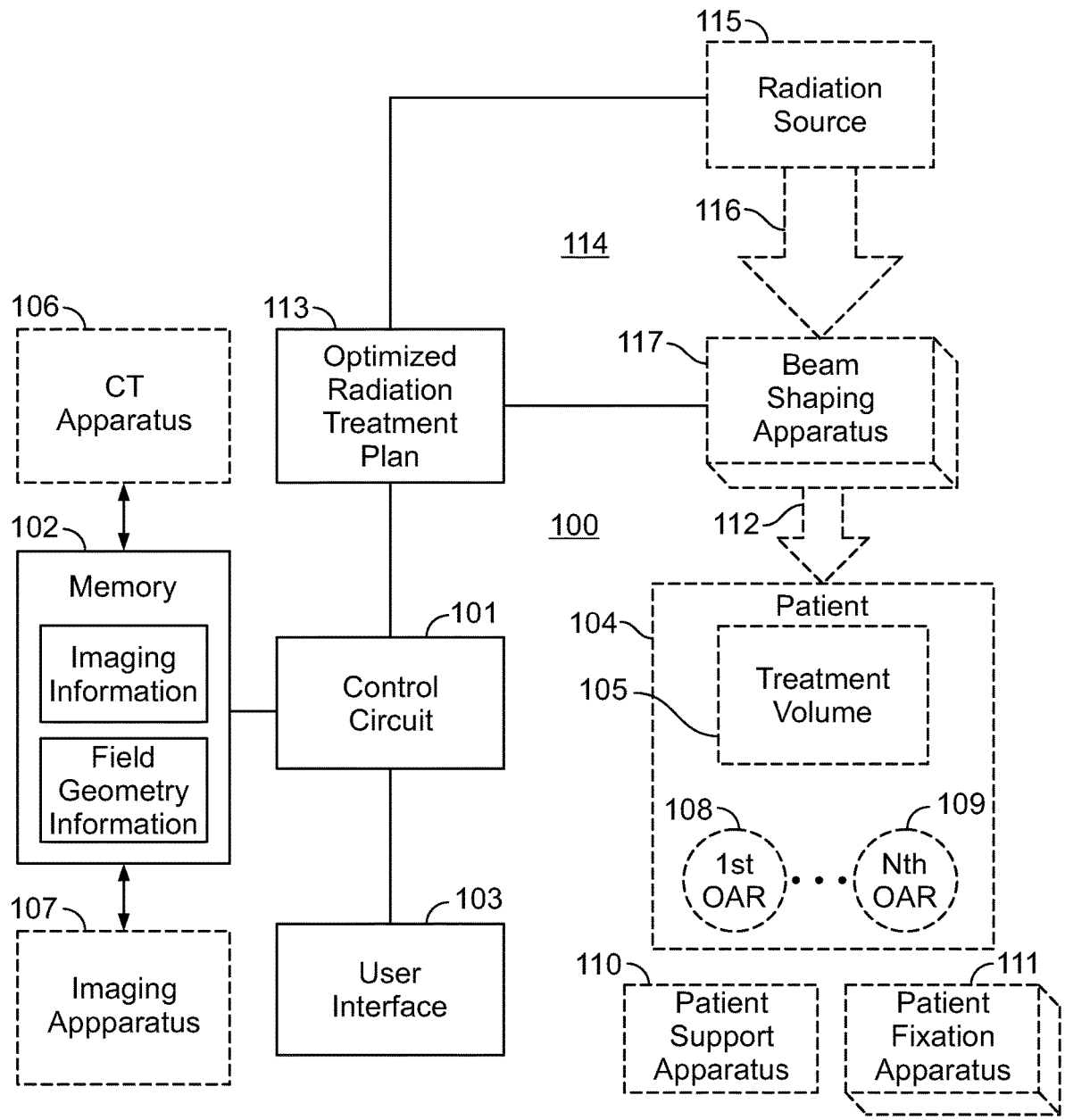
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments serve to facilitate providing a radiation treatment plan to administer therapeutic radiation to a patient via a particular radiation treatment platform by generating a predicted three-dimensional dose map for that radiation treatment plan. That dose map can then be used in various ways to compare and/or vet a given radiation treatment plan to help assess, as one example, whether the plan is ready to utilize when administering therapeutic radiation to a patient. As another example, such a dose prediction can be used to check whether the optimized dose is quite different from what one would expect based on the treatment history data for the corresponding application setting. (Since this dose prediction can be based on only part of the planning information, the teachings can be useful and applicable even at a time when the whole set of planning information may not yet be available.)

By one approach, the foregoing comprises using a control circuit to access image content regarding the patient as well as field geometry information regarding that particular radiation treatment platform. The control circuit then generates the predicted three-dimensional dose map for the radiation treatment plan as a function of both the image content regarding the patient and the field geometry information.

These teachings will accommodate various kinds of image content regarding the patient. Examples include but are not limited to at least one organ mask and at least one computed tomography image. As used herein it will be understood that the one or more organ masks can comprise, for example, a contoured planning target volume mask (to accommodate, for example, a tumor that is located in a region between organs or a tumor that extends across several organs) and/or at least one contoured organ-at-risk mask.

By one approach the aforementioned field geometry information comprises at least one image that graphically represents at least part of the field geometry information. Put another way, at least some of the field geometry information is provided and utilized as an image when generating the predicted three-dimensional dose map. By one approach, the field geometry information that is encoded as imagery is encoded as imagery having a same resolution as, for example, computed tomography images that comprise at least part of the image content regarding the patient. These teachings will accommodate other approaches in these regards as well if desired. As one example, the field geometry information could be encoded as a vector.

By one approach the control circuit is configured to generate the predicted three-dimensional dose map by providing the image content regarding the patient and the field geometry information as input to a convolutional neural network model that processes the field geometry information together with the image content regarding the patient to generate the predicted three-dimensional dose map. In such a case, and by one approach, the image content regarding the patient and the field geometry information can be provided as input to the convolutional neural network model as stacks of two-dimensional images.

The latter can comprise providing the stacks of two-dimensional images via corresponding channels. As an illustrative example in these regards, these channels can comprise, at least in part, a computed tomography images channel, a contoured planning target volume images channel, a contoured organ-at-risk images channel, and a field geometry information channel.

Because such a three-dimensional dose prediction model receives as input the field geometry information in addition to the patient-based imagery, the model can be more readily trained on heterogeneous datasets including data sets that exhibit variations in the location, size, and shape of the planning target volume, thus overcoming that significant technological limitation that characterizes various prior art efforts in these regards. This accommodating capability, in turn, can greatly decrease planning time and/or minimum computational requirements to achieve a useful result within a particular period of time.

In addition, those skilled in the art will appreciate that such a three-dimensional dose prediction model could be trained using both coplanar and non-coplanar treatment plans. As a result, these teachings can support making faster-than-usual comparisons between three-dimensional dose maps predicted with different field geometries and thus help the planner to choose a most suitable field geometry for a radiation treatment plan for a given patient.

These and other benefits may become clearer upon making a thorough review and study of the following detailed description. Referring now to the drawings, and in particular to FIG. 1, an illustrative apparatus 100 that is compatible with many of these teachings will now be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to the aforementioned imaging information and field geometry information, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

In this example the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of the patient-related imaging information described herein.

In this illustrative example the control circuit 101 is configured to ultimately output an optimized radiation treatment plan 113. This radiation treatment plan 113 typically comprises specified values for each of a variety of treatment-platform parameters during each of a plurality of sequential fields. In this case the radiation treatment plan 113 is generated through an optimization process. Various automated optimization processes specifically configured to generate such a radiation treatment plan are known in the art. As the present teachings are not overly sensitive to any particular selections in these regards, further elaboration in these regards is not provided here except where particularly relevant to the details of this description.

By one approach the control circuit 101 can operably couple to a radiation treatment platform 114 that is configured to deliver therapeutic radiation 112 to a corresponding patient 104 in accordance with the optimized radiation treatment plan 113. These teachings are generally applicable for use with any of a wide variety of radiation treatment platforms. In a typical application setting the radiation treatment platform 114 will include radiation source 115. The radiation source 115 can comprise, for example, a radio-frequency (RF) linear particle accelerator-based (linac-based) x-ray source, such as the Varian Linatron M9. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons. A typical radiation treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more beam-shaping apparatuses 117 (such as jaws, multi-leaf collimators, and so forth) to provide selective beam shaping and/or beam modulation as desired. As the foregoing elements and systems are well understood in the art, further elaboration in these regards is not provided here except where otherwise relevant to the description.

Figure 2:
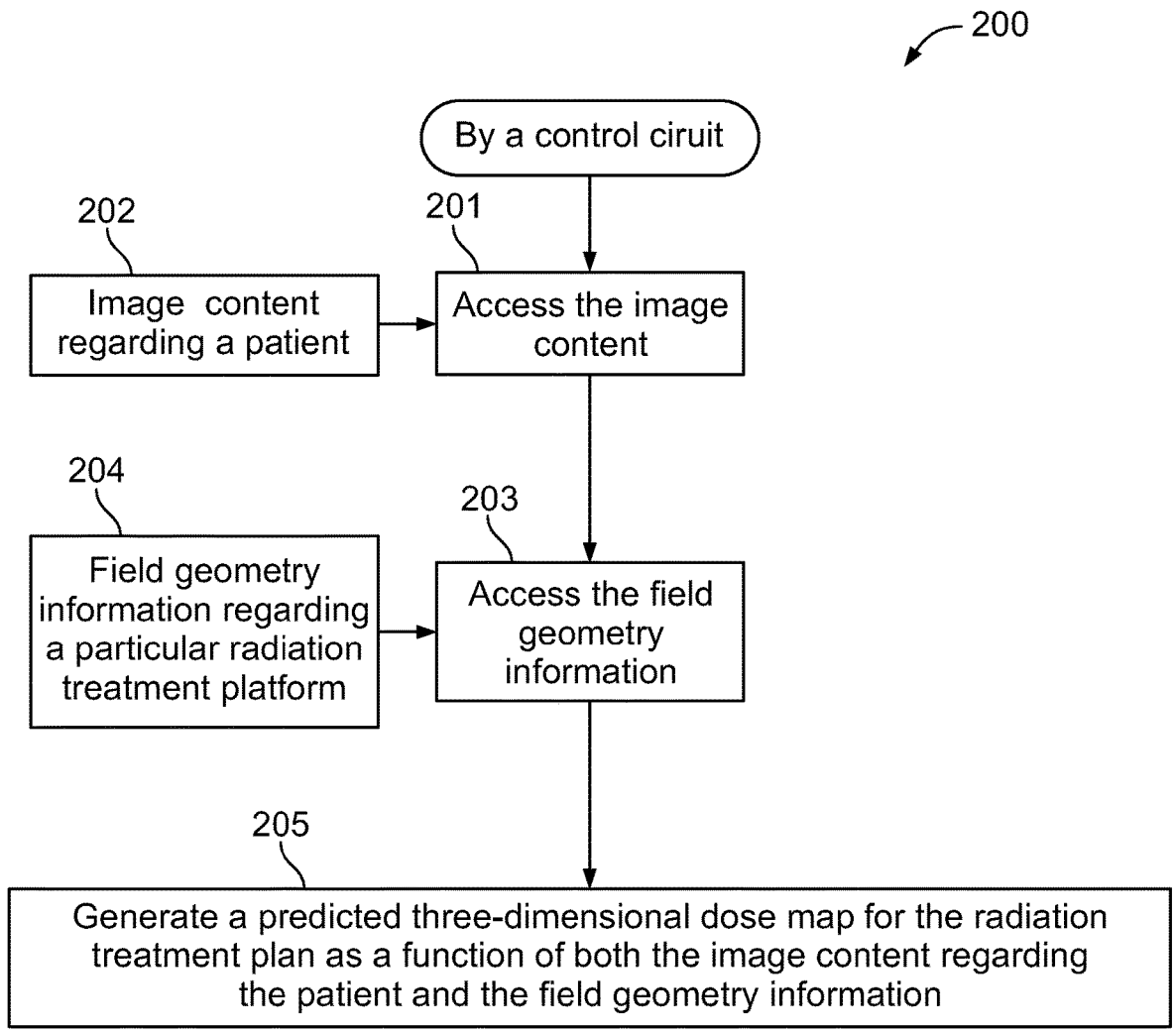
FIG. 2 comprises a flow diagram as configured in accordance with various embodiments of these teachings.

Referring now to FIG. 2, a process 200 that can be carried out, for example, by the above-described control circuit 101 will now be presented.

At block 201, the control circuit 101 accesses the aforementioned memory 102 to thereby access image content 202 regarding the patient. (Those skilled in the art will understand that during the model training phase, likely heterogeneous image content for a large set of different patients having differently-sized and differently-located tumors will be accessed and utilized. The described process presumes use of an already-trained model.) This image content 202 may comprise image content provided by the aforementioned CT apparatus 106 and/or the aforementioned imaging apparatus 107 as desired. In many application settings it will be beneficial for the image content 202 to include one or more computed tomography images, one or more contoured planning target volume images, and one or more contoured organ-at-risk images. (Those skilled in the art will know and understand that important volumes, such as a patient's planned target volume and organs-at-risk, have their respective peripheries visually identified during the planning process to yield so-called contoured images. By one approach these teachings will accommodate presenting the contoured planning target volume(s) and organ(s)-at-risk by use of corresponding organ masks.)

At block 203, the control circuit 101 accesses the aforementioned memory 102 to thereby also access field geometry information 204 particular to a particular radiation treatment platform such as the platform 114 described generally above. Examples of field geometry information 204 include, for example, location positions for the aforementioned radiation source 115 vis-á-vis a gantry and/or some patient reference point such as an isocenter corresponding to the planning treatment volume. Other examples include, but are not limited to, gantry angles, collimator angles, jaw positions, couch angles, and so forth.

Pursuant to these teachings, at least part of the field geometry information is encoded as imagery and therefore comprises at least one image that depicts the corresponding field geometry information. By one approach all of the provided field geometry information 204 comprises one or more such images. In many application settings it can be beneficial for the field geometry information to be encoded as imagery having a same resolution as the computed tomography images provided as part of the above-mentioned image content 202.

It may be noted here that, by one approach, the aforementioned accessed content is heterogeneous patient data for a variety of patients, where the data exhibits variations in the position, shape, and size of the planning treatment volume as well as the type of treatment.

At block 205, the control circuit 101 then generates a predicted three-dimensional dose map for a particular radiation treatment plan as a function of both the image content 202 regarding the patient and the field geometry information 204. (As used herein, the word "predicted" as used with the expression "three-dimensional dose map" will be understood to refer to a three-dimensional radiation dose map that is predicted to result when treating the patient 104 per the field geometry associated with this particular radiation treatment plan.) Accordingly, the predicted three-dimensional dose map will provide predicted levels of radiation dosing at various locations within the relevant planning treatment volume and organs-at-risk. This can comprise, for example, indicating the spatial distribution of varying levels of radiation dose imparted to such patient structures. In the present case it is assumed that the dose map identifies quantitatively and discreetly differing levels of radiation dose within and throughout the segmented, identified patient structures. This can be done using any visually discrete approach, such as by using different colors for different levels of radiation dosing and/or isodose lines as are known in the art.

These teachings will further accommodate, if desired, presenting part or all of the predicted three-dimensional dose map via the aforementioned user interface 103 and/or presenting in some comparative manner and via the user interface 103 two or more predicted three-dimensional dose maps for different radiation treatment plans to facilitate their comparison by a technician, oncologist, or the like. These teachings will also, of course, accommodate using a vetted radiation treatment plan with the radiation treatment platform to administer therapeutic radiation to the patient per the plan.

By one approach the control circuit 101 can be configured to employ deep learning to generate the predicted three-dimensional dose map for the radiation treatment plan. Deep learning (also sometimes referred to as hierarchical learning, deep neural learning, or deep structured learning) is generally defined as a subset of machine learning in artificial intelligence that has networks capable of learning unsupervised from data that is unstructured or unlabeled. That said, deep learning can be also be supervised or semi-supervised if desired. Deep learning architectures include deep neural networks, deep belief networks, recurrent neural networks, and convolutional neural networks.

Figure 3:
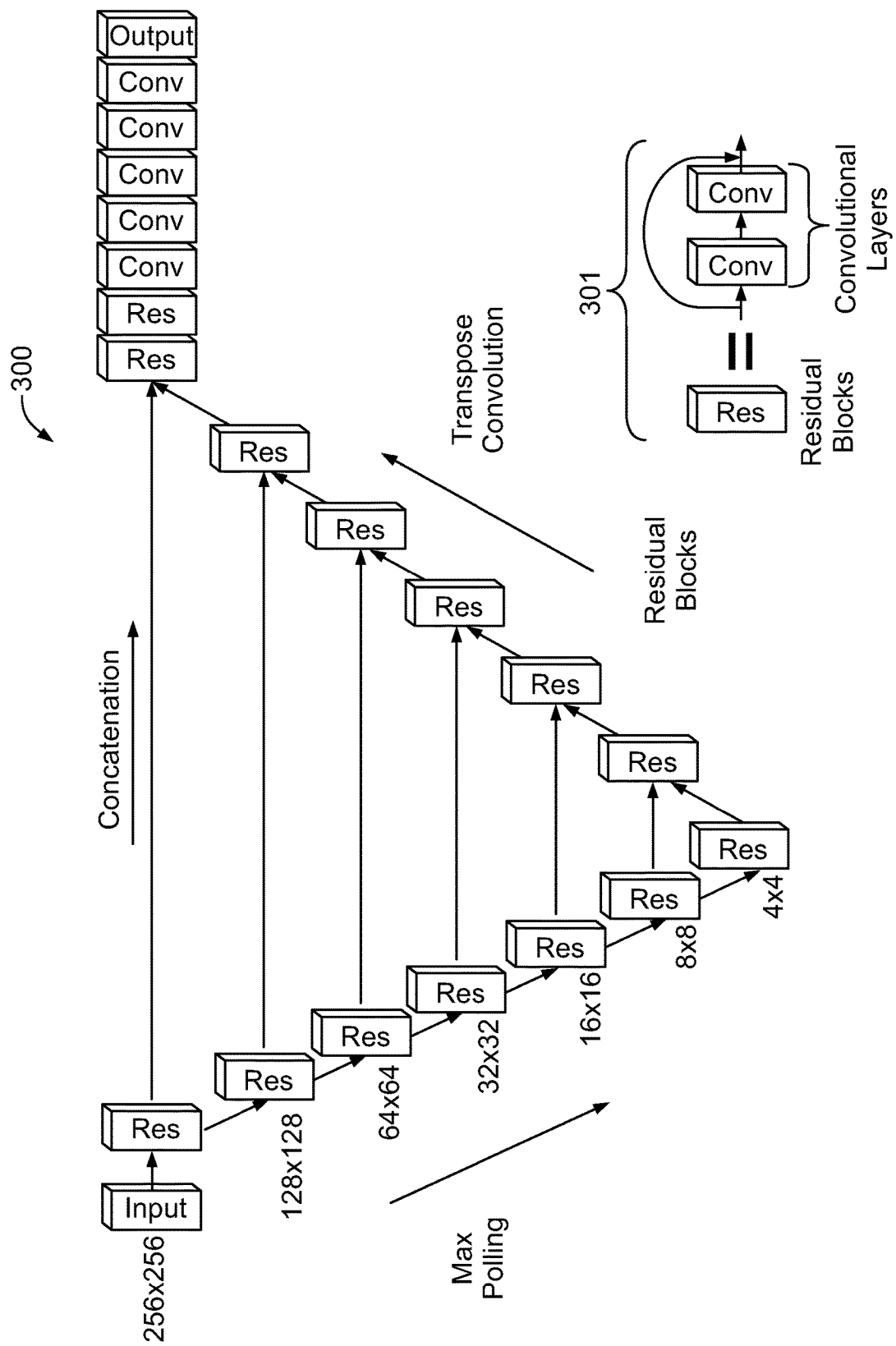
FIG. 3 comprises a neural network processing view as configured in accordance with various embodiments of these teachings.

For the sake of an illustrative example, and without intending to suggest any particular limitations in these regards, it will be presumed here that the control circuit 101 is configured as a convolutional neural network model that receives the aforementioned image content regarding the patient and the field geometry information as input and that processes the field geometry information together with the image content regarding the patient to generate a predicted three-dimensional dose map. FIG. 3 provides a general illustrative example 300 in these regards.

By one approach the control circuit 101 is configured to provide both the image content regarding the patient and the field geometry information as input to the convolutional neural network model as stacks of two-dimensional images and via corresponding channels. (By way of example, these channels may include, at least in part, a computed tomography images channel, a contoured planning target volume images channel, a contoured organ-at-risk images channel, and a field geometry information channel.)

In this example 300 the input of the convolutional neural network model consists of stacks (sometimes also known in the art as cubes) of two-dimensional images. Each two-dimensional image contains several channels corresponding to the aforementioned computer tomography image(s) and the planning treatment volume and organ(s)-at-risk masks. An additional channel for each image carries the field geometry information that is encoded as an image having the same shape and resolution as the computed tomography image(s).

In this illustrative example 300 the network architecture resembles a U-net. (A U-Net is a convolutional neural network that was developed for biomedical image segmentation. Such a network is based on a fully convolutional network having its architecture modified and extended to provide precise segmentations with fewer training images. It will be understood that these teachings are not limited to use with a U-net; instead, any convolutional neural network that can analyze three-dimensional image data can likely serve.) In this example 300, however, the architecture departs from a traditional U-net at least because each level employs residual blocks. As detailed at reference numeral 301, each residual block consists of a stack of two convolutional layers. The output of each residual block is the sum of the input layer and the second convolution.

The input stack for the convolutional neural network model has the shape N×256×256×Ch, where N refers to the number of slices that each have Ch channels of size 256×256 pixels. (As used herein, a "slice" refers to a set containing one CT image, one target image, one organ-at-risk image, and one with field geometry information.) Here, it is presumed that the first (ch-2) channels contain sets of organ masks, the second to last channel contains the corresponding computed tomography image, and the last channel includes the field geometry information image. (It may be noted that the order in which these channels are provided is not necessarily important. What is useful, however, is that this information be provided as input to the network.)

In this illustrative example 300 the output of the network consists of a stack having the shape (n−2)×256×256×1. This stack represents the dose predictions corresponding to the input image stack, excepting the first and last slices.

By one approach the organ-at-risk masks can be grouped together following the implementing clinic's organ importance ranking. The organ-at-risk images can be represented as binary masks with value 1 corresponding to positions belonging to a given organ and value 0 to the positions outside of the organ.

By one approach, and for the planning treatment volume masks, one can use a scaled dose level value for the positions corresponding to a given planning treatment volume and value 0 for any positions outside of the planning treatment volume. For example, the mask corresponding to the planning treatment volume receiving the highest dose level ("PTV_high") can have value 1 for the corresponding pixels located inside the organ. For the mask corresponding to the planning treatment volume receiving the next dose level ("PTV_int") one can use the ratio between the "PTV_high" and "PTV_int" dose levels for the pixels located inside this organ.

As a very specific example, offered for the purposes of illustration, for intensity-modulated radiation therapy (IMRT) treatments the field geometry image can consist, in the simplest case, of just a set of rays starting from the isocenter position and corresponding to the set of field angles used for the particular patient. In a more complex representation, the fields can be illustrated as conical beams starting from an effectively point-like source located in a rotational gantry and covering the target. As another example, for volumetric-modulated arc therapy (VMAT) treatments the field geometry image may consist of both the corresponding arcs and the intensity levels.

These teachings are highly flexible in practice and will accommodate any of a variety of modifications to the foregoing. As one example in these regards, the field geometry information can be given to the network as a separate stack in addition to the stack that contains the computed tomography images and the planning treatment volume and organ masks. Such a configuration would allow the two stacks to be processed in parallel by the first few layers of the network. Then, the extracted features could be pulled together (for example, by concatenation) and processed further by the rest of the network.

As another example, when training the model on cases using coplanar field geometries, an alternative way of presenting the field geometry information to the convolutional neural network model is as a 360-dimensional vector. For IMRT treatments, one could put non-zero values on the positions corresponding to the gantry angles and zeros everywhere else. For VMAT treatments one can have non-zero blocks corresponding to the treatment arcs. This vector can be merged with lower-level features extracted from the image cube, e.g., on the bottom level of the above-referenced U-net, and the union will be processed together by the rest of the network.

Because this approach to predicting a three-dimensional dosing map receives field geometry information as input, it can be successfully and even efficiently trained on heterogeneous datasets that exhibit variations in the location, size, and shape of planning treatment volumes. These differences are the ones which, in turn, can lead to the use of different treatment field geometry types (e.g., sided or full arc treatment) as well as different field positions. Furthermore, the described prediction model could be trained using both coplanar and non-coplanar treatment plans. Accordingly, these teachings can be used to make quick comparisons between three-dimensional dose maps predicted with different field geometries and thus help the planner to choose the most suitable field geometry for a given patient using a particular radiation treatment platform.

It may be especially appreciated that these teachings do not require that a full radiation treatment plan be defined (for example, a plan that specifies a complete leaf sequence for the anticipated multi-leaf collimator) when training and/or using the dose prediction model.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. An apparatus to facilitate providing a radiation treatment plan to administer therapeutic radiation to a patient via a particular radiation treatment platform, the apparatus comprising:
    a memory having image content regarding the patient and field geometry information regarding the particular radiation treatment platform stored therein;
    a control circuit operably coupled to the memory, the control circuit being configured to:
        access the image content regarding the patient;
        access the field geometry information;
        generate a predicted three-dimensional dose map that will result when treating the patient with the radiation treatment plan as a function of both the image content regarding the patient and the field geometry information, wherein the predicted three-dimensional dose map identifies quantitatively and discreetly differing levels of radiation dose within and throughout at least part of segmented, identified structures.

2. The apparatus of claim 1 wherein the image content regarding the patient comprises, at least in part, at least one organ mask and at least one computed tomography image.

3. The apparatus of claim 2 wherein the at least one organ mask comprises, at least in part, a contoured planning target volume and at least one contoured organ-at-risk.

4. The apparatus of claim 1 wherein the field geometry information comprises at least one image depicting at least part of the field geometry information.

5. The apparatus of claim 1 wherein the control circuit is configured to generate the predicted three-dimensional dose map by providing the image content regarding the patient and the field geometry information as input to a convolutional neural network model that processes the field geometry information together with the image content regarding the patient to generate the predicted three-dimensional dose map.

6. The apparatus of claim 5 wherein the control circuit is configured to provide the image content regarding the patient and the field geometry information as input to the convolutional neural network model as stacks of two-dimensional images.

7. The apparatus of claim 6 wherein the control circuit is configured to provide the stacks of two-dimensional images via corresponding channels.

8. The apparatus of claim 7 wherein the channels comprise, at least in part:
    a computed tomography images channel;
    a contoured planning target volume images channel;
    a contoured organ-at-risk images channel; and
    a field geometry information channel.

9. The apparatus of claim 8 wherein the field geometry information provided via the field geometry information channel is encoded as imagery.

10. The apparatus of claim 9 wherein the field geometry information that is encoded as imagery is encoded as imagery having a same resolution as the computed tomography images.

11. A method to facilitate providing a radiation treatment plan to administer therapeutic radiation to a patient via a particular radiation treatment platform, the method comprising:
    providing a memory having image content regarding the patient and field geometry information regarding the particular radiation treatment platform stored therein; and
    by a control circuit operably coupled to the memory:
        accessing the image content regarding the patient;
        accessing the field geometry information; and
        generating a predicted three-dimensional dose map that will result when treating the patient with the radiation treatment plan as a function of both the image content regarding the patient and the field geometry information, wherein the predicted three-dimensional dose map identifies quantitatively and discreetly differing levels of radiation dose within and throughout at least part of segmented, identified structures.

12. The method of claim 11 wherein the image content regarding the patient comprises, at least in part, at least one organ mask and at least one computed tomography image.

13. The method of claim 12 wherein the at least one organ mask comprises, at least in part, a contoured planning target volume and at least one contoured organ-at-risk.

14. The method of claim 11 wherein the field geometry information comprises at least one image depicting at least part of the field geometry information.

15. The method of claim 11 wherein generating the predicted three-dimensional dose map comprises providing the image content regarding the patient and the field geometry information as input to a convolutional neural network model that processes the field geometry information together with the image content regarding the patient to generate the predicted three-dimensional dose map.

16. The method of claim 15 wherein providing the image content regarding the patient and the field geometry information as input to the convolutional neural network model comprises providing the image content regarding the patient and the field geometry information as input to the convolutional neural network model as stacks of two-dimensional images.

17. The method of claim 16 wherein providing the stacks of two-dimensional images comprises providing the stacks of two-dimensional images via corresponding channels.

18. The method of claim 17 wherein the channels comprise, at least in part:
    a computed tomography images channel;
    a contoured planning target volume images channel;
    a contoured organ-at-risk images channel; and
    a field geometry information channel.

19. The method of claim 18 wherein the field geometry information provided via the field geometry information channel is encoded as imagery.

20. The method of claim 19 wherein the field geometry information that is encoded as imagery is encoded as imagery having a same resolution as the computed tomography images.

* * * * *